US012752126B2

(12) United States Patent
Luo

(10) Patent No.: US 12,752,126 B2
(45) Date of Patent: Oct. 6, 2026

(54) LAMP BODY BRACKET DEVICE

(71) Applicant: Dongguan Laiguang Electronic Technology Co., Ltd., Dongguan (CN)

(72) Inventor: Zekai Luo, Dongguan (CN)

(73) Assignee: Dongguan Laiguang Electronic Technology Co., Ltd., Dongguan (CN)

( * ) Notice: Subject to any disclaimer, the term of this patent is extended or adjusted under 35 U.S.C. 154(b) by 0 days.

(21) Appl. No.: 19/326,814

(22) Filed: Sep. 12, 2025

(65) Prior Publication Data

US 2026/0007901 A1 Jan. 8, 2026

(51) Int. Cl.
*A61N 5/06* (2006.01)

(52) U.S. Cl.
CPC ........ *A61N 5/06* (2013.01); *A61N 2005/0633* (2013.01); *A61N 2005/0654* (2013.01)

(58) Field of Classification Search
CPC .............. A61N 5/06; A61N 2005/0633; A61N 2005/0654; F16M 11/28; B25H 1/0007; F21L 14/04
USPC ..... 248/274.1, 161, 405; 269/104, 140, 296; 362/413–414
See application file for complete search history.

(56) References Cited

U.S. PATENT DOCUMENTS 2,786,372 A * 3/1957 Lassy ........................ B25B 1/12 D8/74
2,803,872 A * 8/1957 Massa .................... F16M 11/12 269/106
2,827,690 A * 3/1958 Brown ................... F16M 11/10 269/62
6,024,348 A * 2/2000 Ventura ............... B05B 13/0285 269/104
6,131,870 A * 10/2000 Tseng ....................... A47B 9/04 248/405
7,448,606 B1 * 11/2008 Johnson .............. B05B 13/0285 269/16
2007/0022950 A1 * 2/2007 Livingston .......... B05B 13/0285 248/128
2016/0023229 A1 * 1/2016 Johnson ............... B25H 1/0007 269/152

FOREIGN PATENT DOCUMENTS

| | | |
|---|---|---|
| CN | 206434717 A | 8/2017 |
| CN | 215135988 A | 12/2021 |
| CN | 218979209 A | 5/2023 |
| CN | 219050145 A | 5/2023 |

* cited by examiner

*Primary Examiner* — Christopher Garft

(57) ABSTRACT

A lamp body bracket device includes a base, a lifting seat and a clamping assembly. The base can be placed on a ground, a tabletop or a support surface; the lifting seat is connected to the base and is liftable and can lift along the up and down direction. The lifting seat is provided with a support portion. The clamping assembly includes a support bracket and at least one clamping member. The support bracket is connected to the support portion, and provided horizontally or vertically relative to the support portion. A height position of the support bracket is adjusted along with the lifting of the lifting seat. The clamping member is provided on the support bracket and a position of the clamping member can be adjusted relative to the support bracket. The clamping member is provided with a clamping groove for clamping the lamp body.

12 Claims, 7 Drawing Sheets

LAMP BODY BRACKET DEVICE

CROSS-REFERENCE TO RELATED APPLICATIONS

This application claims priority to a Chinese Application No. 202521646460.1, filed on Aug. 4, 2025, titled "Lamp Body Bracket Device", the entire contents of which are hereby incorporated herein by reference in their entirety.

TECHNICAL FIELD

The present application relates to the technical field of lamp body bracket devices, in particular to a lamp body bracket device.

BACKGROUND

With the development of science and technology, lamp body bracket devices have been applied in people's lives and are used to support external lamp bodies, such as physiotherapy lamps or phototherapy lamps. These bracket devices support physiotherapy lamps or phototherapy lamps. In the existing technology, the conventional lamp body bracket device consists of a base, a support bracket and a clamping member. The support bracket is connected to the base, and the clamping member is attached to the support bracket. The clamping member is used to clamp lamp bodies of a uniform size. However, the clamping member cannot be lifted, lowered or moved, resulting in poor versatility of the existing lamp body bracket devices.

SUMMARY

The purpose of this present application is to provide a lamp body bracket device. The base can be placed on a ground, a tabletop or a support surface; the lifting seat is provided above the base, and the lifting seat is connected to the base and is liftable and can lift along the up and down direction. The lifting seat is provided with a support portion. The clamping assembly includes a support bracket and at least one clamping member. The support bracket is provided on one side of the support portion, connected to the support portion, and provided horizontally or vertically relative to the support portion. A height position of the support bracket is adjusted along with the lifting of the lifting seat. The clamping member is provided on the support bracket and a position of the clamping member can be adjusted relative to the support bracket. The clamping member is provided with a clamping groove for clamping the lamp body, so as to realize the functions of lifting, moving and clamping, thereby facilitating the lamp body to be suspended in the air or placed on the ground, to be compatible with different supporting scenarios of the lamp body. And the clamping member adjusts the size of the clamping groove during movement to adapt to lamp bodies of various sizes, thereby improving the versatility of the lamp body bracket device.

To achieve the above purpose, the present application provides the following technical solutions: a lamp body bracket device, for supporting a lamp body, including:

- a base, capable of being placed on a ground, a table top or a support surface;
- a lifting seat, provided above the base, wherein the lifting seat is connected to the base, is liftable and lifts along an up and down direction, and the lifting seat is provided with a support portion; and
- a clamping assembly, comprising a support bracket and at least one clamping member, wherein the support bracket is provided on a side of the support portion, connected to the support portion and provided horizontally or vertically relative to the support portion;
- wherein a height position of the support bracket is adjusted along with a lifting of the lifting seat, and the at least one clamping member is provided on the support bracket and a position of the at least one clamping member is adjusted relative to the support bracket, and the clamping member is provided with a clamping groove for clamping the lamp body.

BRIEF DESCRIPTION OF THE DRAWINGS

To clarify the technical solutions in the embodiments of the present application, the accompanying drawings required for describing the embodiments will be briefly introduced below. Obviously, the drawings in the following description are only some embodiments of the present application. For those skilled in the art, other drawings can also be obtained based on these drawings without creative work.

For a more complete understanding of the present application and its beneficial effects, the following description will be made in conjunction with the accompanying drawings. In the following description, the same reference numerals denote the same parts.

DETAILED DESCRIPTION OF THE EMBODIMENTS

The technical solutions in the embodiments of the present application will be clearly and completely described below in conjunction with the accompanying drawings in the embodiments of the present application. Obviously, the described embodiments are only a part of the embodiments of the present application, rather than all the embodiments. Based on the embodiments in the present application, all other embodiments obtained by those skilled in the art without creative work shall fall within the protection scope of the present application.

Figure 1:
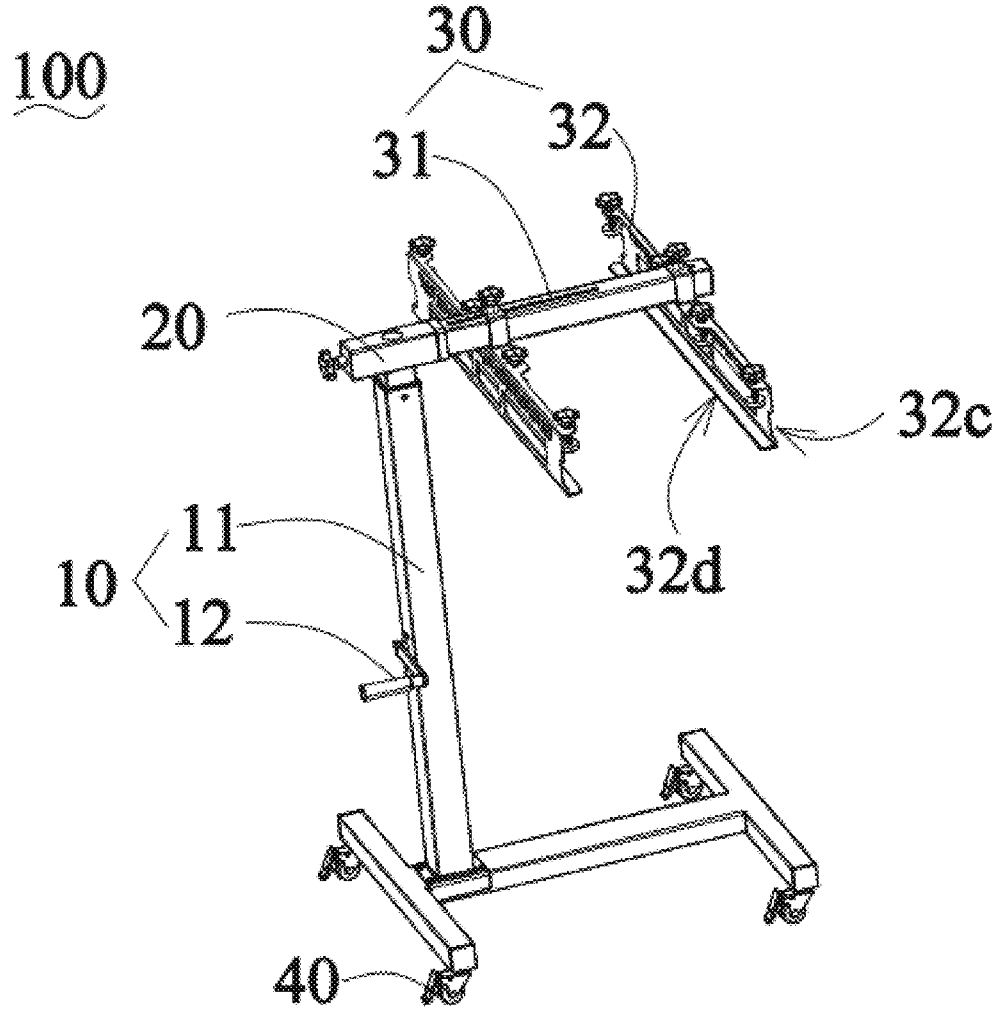
FIG. 1 is a schematic diagram of a bracket assembly according to an embodiment of the present application.
Figure 2:
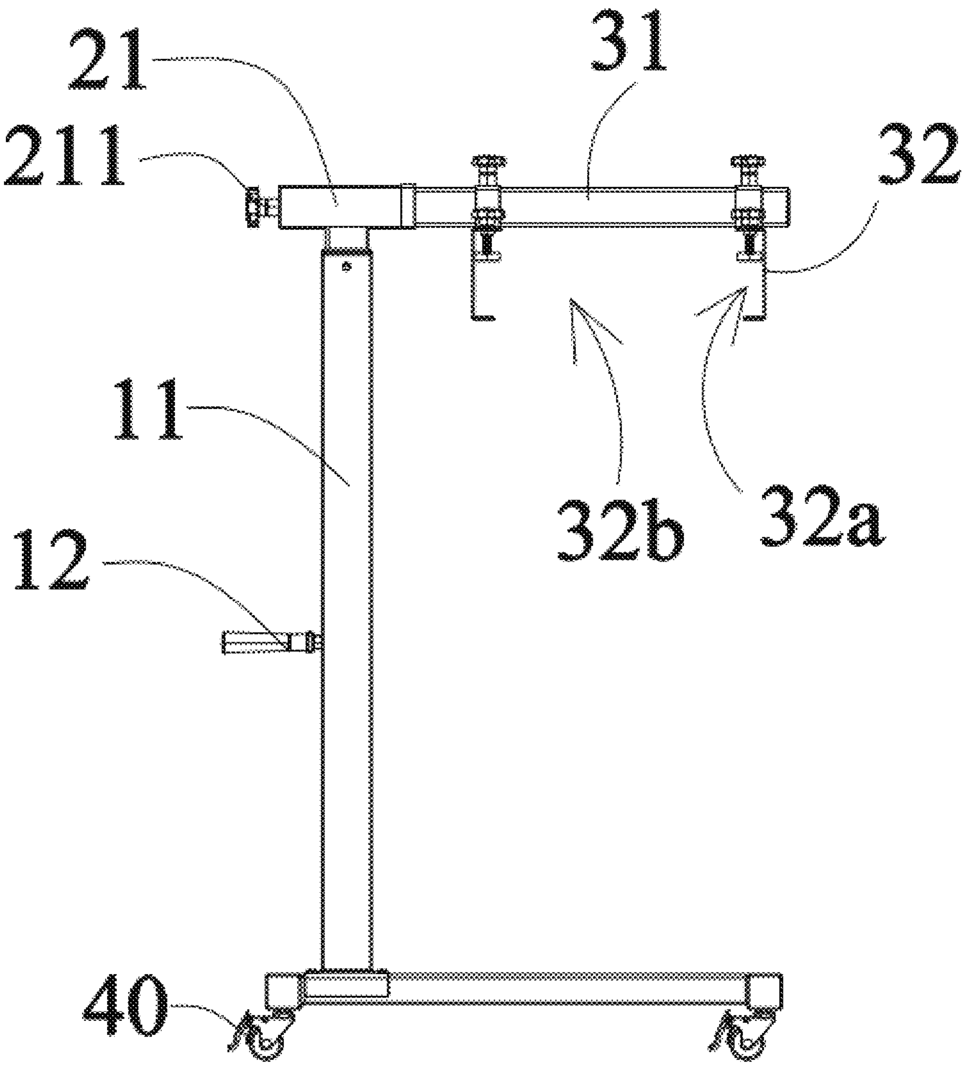
FIG. 2 is a side view of the bracket assembly according to an embodiment of the present application.
Figure 3:
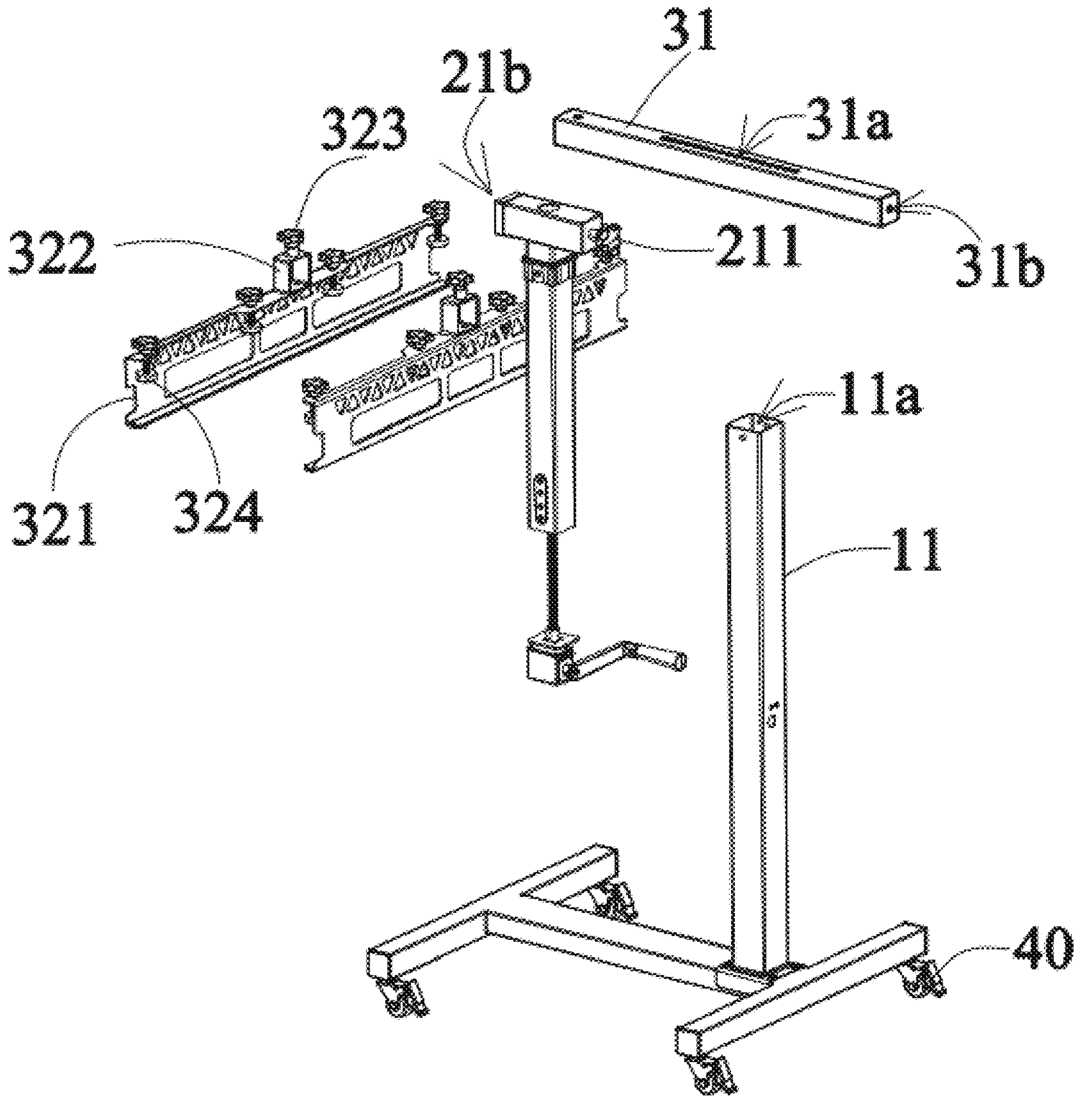
FIG. 3 is an exploded view of the bracket assembly according to an embodiment of the present application.
Figure 4:
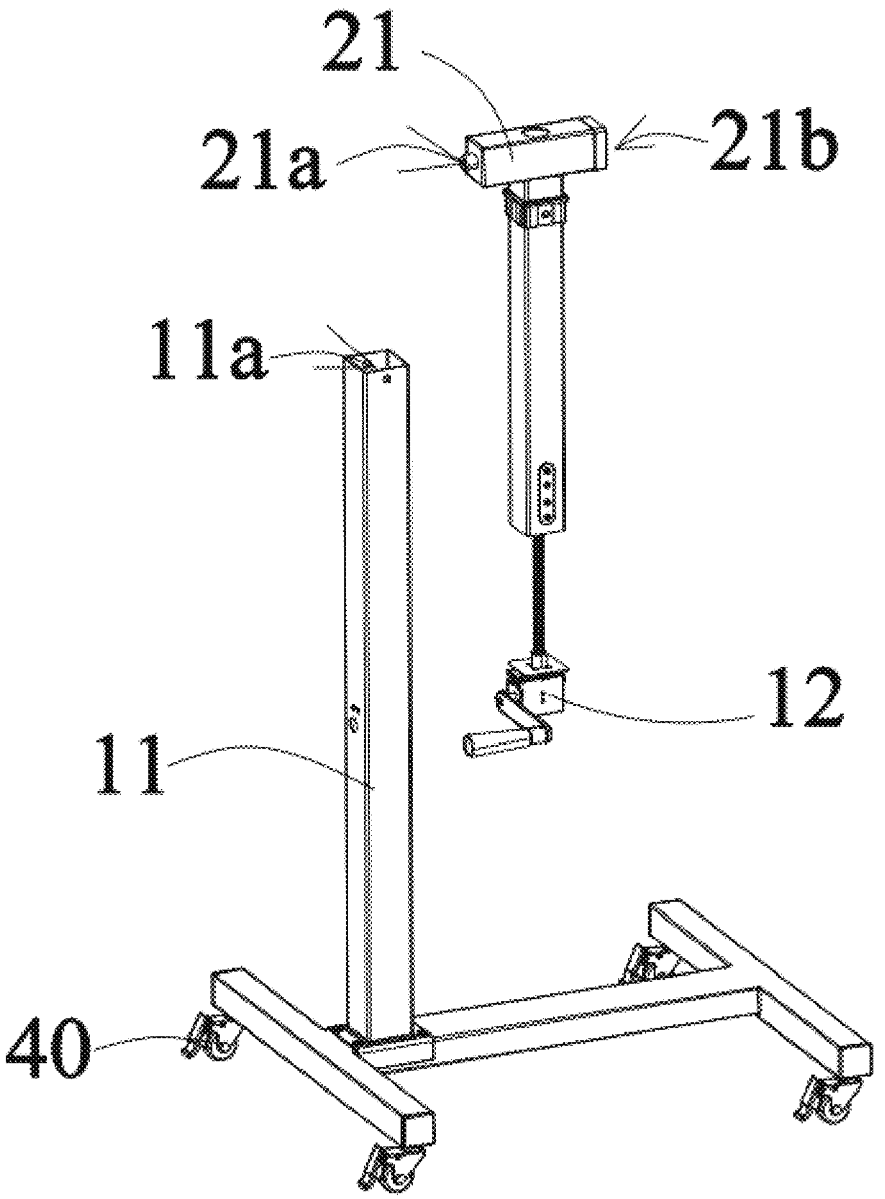
FIG. 4 is an exploded view of a base and a lifting seat of the bracket assembly according to an embodiment of the present application.
Figure 5:
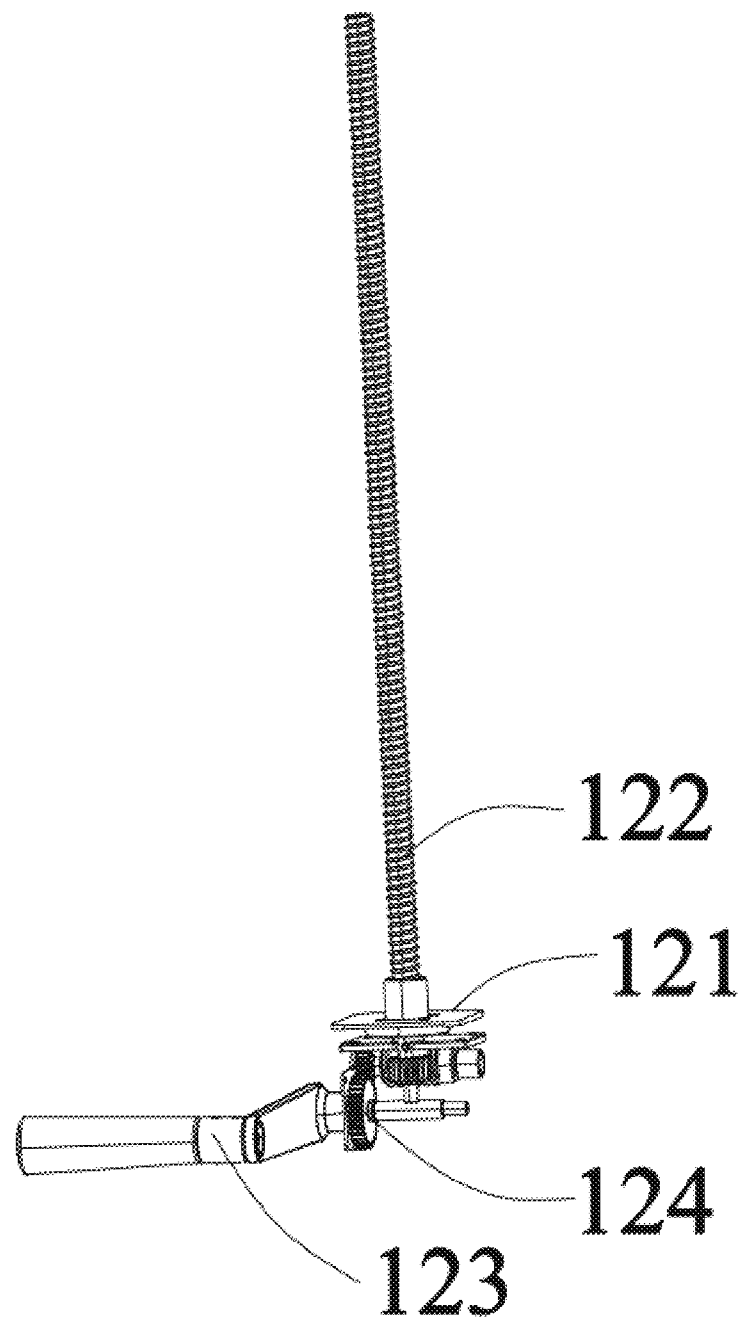
FIG. 5 is a schematic diagram of an internal structure of a lifting module of the bracket assembly according to an embodiment of the present application.
Figure 6:
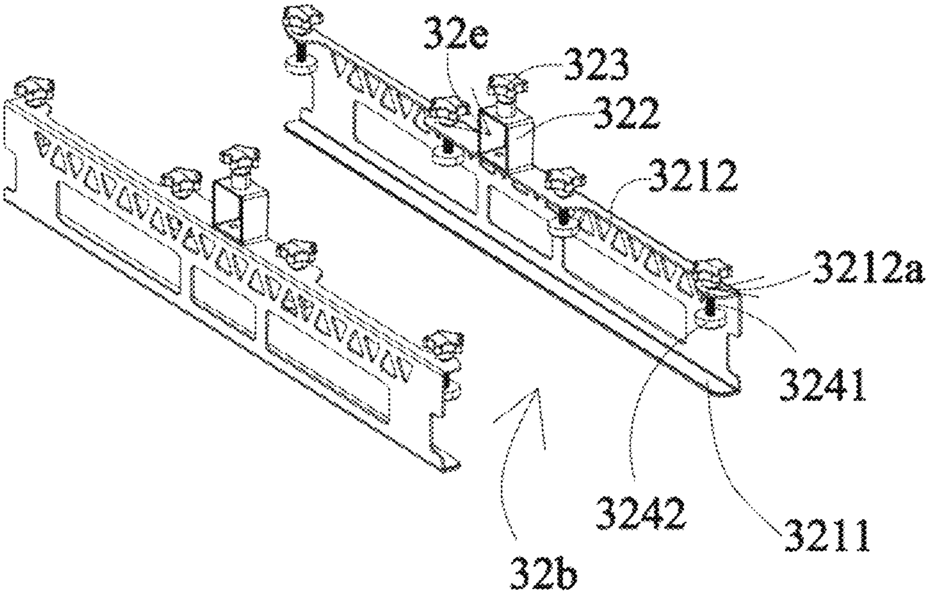
FIG. 6 is a schematic diagram of a clamping member of the bracket assembly according to an embodiment of the present application.
Figure 7:
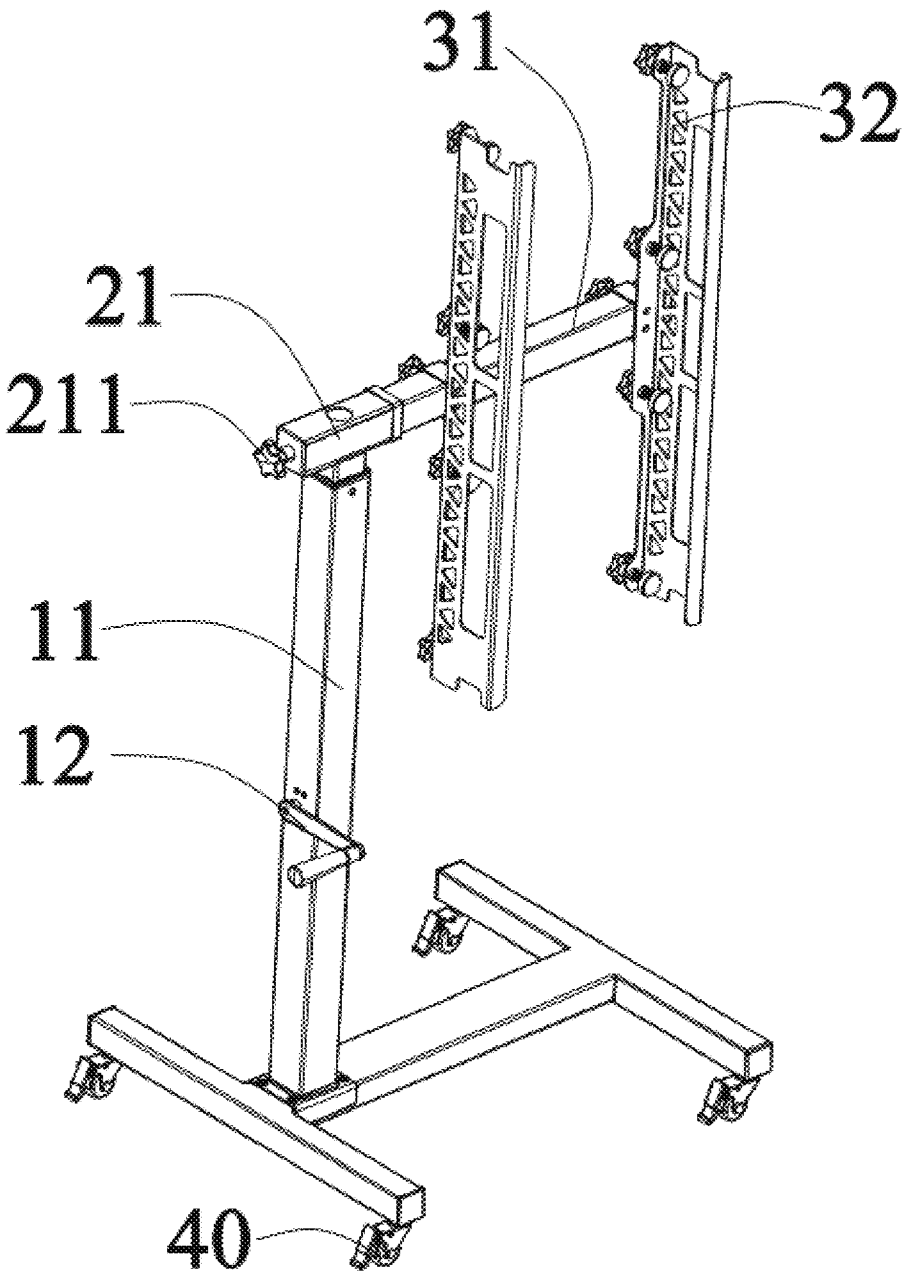
FIG. 7 is a schematic diagram of a support bracket of the bracket assembly in a vertical arrangement according to an embodiment of the present application.

Please refer to FIGS. 1 to 7. The present application provides a lamp body bracket device 100. The lamp body bracket device 100 is used to support external electronic components, which can be phototherapy components or physiotherapy components.

Please refer to FIGS. 1 to 7, in the embodiment of the present application, the lamp body bracket device 100 includes a base 10, a lifting seat 20 and a clamping assembly 30. The base 10 can be placed on a ground, a tabletop or a support surface. The lifting seat 20 is provided above the base 10, and the lifting seat 20 is connected to the base 10 and is liftable and can lift along the up and down direction. The lifting seat 20 is provided with a support portion 21. The clamping assembly 30 includes a support bracket 31 and at least one clamping member 32. The support bracket 31 is provided on one side of the support portion 21, connected to the support portion 21, and provided horizontally or vertically relative to the support portion 21. A height position of the support bracket 31 is adjusted along with the lifting of the lifting seat 20. The clamping member 32 is provided on the support bracket 31 and a position of clamping member 32 can be adjusted relative to the support bracket 31. The clamping member 32 is provided with a clamping groove 32*a* for clamping the lamp body, so as to realize the functions of lifting, moving and clamping, which facilitates the lamp body to be suspended in the air or placed on the ground, compatible with different supporting scenarios of the lamp body. And the clamping member 32 adjusts the size of the clamping groove 32*a* during the movement to adapt to lamp bodies of various sizes, thereby improving the versatility of the lamp body bracket device 100.

Please refer to FIGS. 1 to 7, in the embodiment of the present application, the base 10 serves as the support component of the lamp body bracket device 100, and the base 10 is used to support the lifting seat 20 and the clamping assembly 30. The base 10 can be placed on the ground, the tabletop or the support surface, so that the lamp body bracket device 100 can be stably placed on the ground, the tabletop or the support surface.

The lifting seat 20 is provided above the base 10, and the lifting seat 20 is connected to the base 10 and is liftable, and can lift along the up and down direction, so as to adjust the height position of the lifting seat 20 relative to the base 10. The lifting seat 20 is provided with a support portion 21.

The clamping assembly 30 includes a support bracket 31 and at least one clamping member 32. The support bracket 31 is provided on one side of the support portion 21, connected to the support portion 21, and provided horizontally or vertically relative to the support portion 21, so that the clamping assembly 30 can be connected to the lifting seat 20 through the cooperation of the support bracket 31 and the support portion 21. A height position of the support bracket 31 is adjusted along with the lifting of the lifting seat 20. The clamping member 32 is provided on the support bracket 31 and a position of the clamping member 32 can be adjusted relative to the support bracket 31. The clamping member 32 is provided with a clamping groove 32*a* for clamping the lamp body, so as to realize the functions of lifting, moving and clamping, which facilitates the lamp body to be suspended in the air or placed on the ground, compatible with different supporting scenarios of the lamp body. And the clamping member 32 adjusts the size of the clamping groove 32*a* during the movement to adapt to lamp bodies of various sizes, thereby improving the versatility of the lamp body bracket device 100.

Please refer to FIGS. 1 to 7, in the embodiment of the present application, there are two clamping members 32, which are provided opposite to each other and provided on the same support bracket 31. The two clamping members 32 are respectively located at different positions of the support bracket 31 to be compatible with lamp bodies of different sizes. The clamping effect of the clamping members 32 on the lamp body is enhanced by two clamping members 32, so as to support lamp bodies of different sizes.

In the two clamping members 32, an accommodation space 32*b* is formed between two opposite clamping grooves 32*a*. The accommodation space 32*b* is used to accommodate the lamp body and allow the lamp body to be inserted in the horizontal direction. The size of the accommodation space 32*b* is adjusted with the movement of the clamping members 32, so that the accommodation space 32*b* can be adapted to lamp bodies of different sizes.

Please refer to FIGS. 1 to 7, in the embodiment of the present application, the clamping member 32 includes a clamping main body 321 and a first installation portion 322. The first installation portion 322 is connected to the clamping main body 321 and provided on the support bracket 31. The first installation portion 322 can be provided at different positions of the support bracket 31, so as to adjust the size of the accommodation space 32*b* by adjusting the position of the first installation portion 322 relative to the support bracket 31.

The clamping main body 321 is supported by the first installation portion 322 and provided below or above the support bracket 31. The clamping main body 321 is provided with a clamping groove 32*a*, and the clamping groove 32*a* has a first opening 32*c* in the left-right direction and a second opening 32*d* in the front-rear direction. Both the first opening 32*c* and the second opening 32*d* are connected to the clamping groove 32*a* and used for the lamp body to pass through, so that the lamp body can enter the clamping groove 32*a* through the first opening 32*c* or the second opening 32*d*, thereby improving the support of the inner side wall of the clamping groove 32*a* to the lamp body and preventing the lamp body from easily disengaging the accommodation space 32*b*.

Please refer to FIGS. 1 to 6, in the embodiment of the present application, the support bracket 31 is provided with a plurality of first threaded holes 31*a*, which are provided along a length direction of the support bracket 31 and distributed at different positions of the support bracket 31. The first installation portion 322 is frame-shaped and sleeved on an outer peripheral side of the support bracket 31. A first through hole 32*e* is provided between the first installation portion 322 and the clamping main body 321, and the first through hole 32*e* is used for the support bracket 31 to pass through, so that the support bracket 31 can support the first installation portion 322 and the clamping main body 321 through the space of the first through hole 32*e*.

The first installation portion 322 is connected with a first screw 323, which passes through the first installation portion 322 and is screwed into the first threaded hole 31*a* to realize the installation of the first installation portion 322 and the support bracket 31, so that the first screw 323 can lock or loosen the first installation portion 322 and the support bracket 31. When the first screw 323 is in a loose state, the clamping member 32 can move relative to the support bracket 31, so as to adjust the size of the accommodation space 32*b*. When the first screw 323 is in a locked state, the clamping effect of the clamping member 32 on the lamp body is ensured, and the lamp body is prevented from shaking.

Please refer to FIGS. 1 to 6, in the embodiment of the present application, the clamping main body 321 is provided with a first support arm 3211 and a second support arm 3212, which are provided opposite to each other in the up and down direction, and a clamping groove 32*a* is formed between the first support arm 3211 and the second support arm 3212. The first support arm 3211 is provided on a lower side of the second support arm 3212 and supports the lamp body in the clamping groove 32*a*, so that the first support arm 3211 and the second support arm 3212 can respectively restrict the movement of the lamp body in the up and down direction.

Please refer to FIGS. 1 to 6, in the embodiment of the present application, the clamping main body 321 is connected with a plurality of pressing members 324, which are provided on the same second support arm 3212 and distributed at different positions of the second support arm 3212. The pressing effect of the second support arm 3212 on the lamp body is enhanced by the plurality of pressing members 324, so as to avoid the loss of pressing effect due to the failure of one pressing member 324.

The pressing member 324 is provided with a moving portion 3241 and a pressing portion 3242. The moving portion 3241 is movably connected to the second support arm 3212 and can move in the up and down direction, so that a height of the pressing member 324 can be adjusted relative to the second support arm 3212 through the moving portion 3241. The pressing portion 3242 is connected to the moving portion 3241 and located in the clamping groove 32*a*. The pressing portion 3242 moves along with the movement of the moving portion 3241 and presses down the lamp body in the clamping groove 32*a*, so that the pressing portion 3242 and the first support arm 3211 jointly clamp the lamp body in the clamping groove 32*a*, so as to adapt to lamp bodies of different heights by adjusting a distance between the pressing portion 3242 and the first support arm 3211, ensuring the clamping effect of the pressing portion 3242 and the first support arm 3211 on the lamp body.

Please refer to FIGS. 1 to 6, in the embodiment of the present application, the second support arm 3212 is provided with a second threaded hole 3212*a*, the moving portion 3241 passes through the second threaded hole 3212*a*, and a peripheral side wall of the moving portion 3241 is screwed into the second threaded hole 3212*a*. The moving portion 3241 is rotated by manual operation, moves relative to the second support arm 3212 and drives the pressing portion 3242 to press the lamp body in the clamping groove 32*a*. An end of the moving portion 3241 located outside the second support arm 3212 serves as the first operating end, so that the moving portion 3241 and the second support arm 3212 can realize the lifting effect of the moving portion 3241 through threaded connection, thereby facilitating the user to adjust the height of the moving portion 3241 by operating the first operating end.

Please refer to FIGS. 1 to 4, in the embodiment of the present application, the support portion 21 is provided with a second through hole 21*a* extending along the length direction of the support portion 21, and the second through hole 21*a* is provided with a front opening 21*b* for the support bracket 31 to pass through. An outer side wall of the support bracket 31 is restricted by an inner side wall of the second through hole 21*a* to maintain the current posture of the support bracket 31, so that the support bracket 31 is provided horizontally relative to the support portion 21.

An end of the support bracket 31 far away from the clamping member 32 is provided with a third threaded hole 31*b*. The support portion 21 is connected with a second screw 211, which passes through the support portion 21 and is screwed into the third threaded hole 31*b*, so that the end of the second screw 211 and the support bracket 31 are clamped on the support portion 21, so that the support portion 21 and the support bracket 31 can be locked by the second screw 211.

Please refer to FIGS. 1 to 5, in the embodiment of the present application, the base 10 is connected with a support column 11, which is provided with a lifting hole 11*a*, that is provided in the up and down direction for the lifting seat 20 to lift, so that the lifting seat 20 can lift relative to the support column 11 through the lifting hole 11*a*, ensuring the lifting effect of the lifting seat 20.

The support column 11 is connected with a lifting module 12 for driving the lifting of the lifting seat 20, so that the user can operate the lifting module 12 to adjust the height of the lifting seat 20. The lifting module 12 is a pneumatic lifting module, a hydraulic lifting module or a mechanical lifting module.

When the lifting module 12 is a mechanical lifting module, the lifting module 12 is provided with a fixing seat 121, a screw rod 122 and a rotation handle 123. The fixing seat 121 is built in the support column 11 and fixed to the support column 11, so that the lifting module 12 can be connected to the support column 11 through the fixing seat 121. The screw rod 122 is rotatably connected to the fixing seat 121 and can rotate along the axis of the screw rod 122. The screw rod 122 is screwed into the lifting seat 20, and the screw rod 122 drives the lifting seat 20 to lift during rotation.

The rotation handle 123 is provided on an outer side of the support column 11 and rotatably connected to the fixing seat 121. A transmission module 124 is provided between the rotation handle 123 and the screw rod 122, and the transmission module 124 is respectively connected to the rotation handle 123 and the screw rod 122 and transmits the power of the rotation handle 123 to the screw rod 122, so that the screw rod 122 rotates under the drive of the rotation handle 123, facilitating the user to adjust the height of the lifting seat 20 by operating the rotation handle 123 and improving the convenience of lifting the lifting seat 20. Optionally, the transmission module 124 is a gear transmission module.

Please refer to FIGS. 1 to 4, the lamp body bracket device 100 further includes a plurality of moving wheels 40, which are respectively connected to four corners of the base 10 and move relative to the ground, so that the lamp body bracket device 100 can be transferred relative to the ground. Optionally, the moving wheels 40 are movable casters with brakes.

In the second embodiment of the present application, the second support arm 3212 is provided with a first via hole, the moving portion 3241 movably passes through the first via hole and can move in the up and down direction, so that the moving portion 3241 can lift relative to the second support arm 3212 through the space of the first via hole. An end of the moving portion 3241 located outside the second support arm 3212 serves as the second operating end, and the second operating end cooperates with the pressing portion 3242 to prevent the moving portion 3241 from disengaging the second support arm 3212. The moving portion 3241 is sleeved with an elastic member, which is located between the second support arm 3212 and the pressing portion 3242 and exerts elastic downward pressure on the pressing portion 3242, so that the pressing portion 3242 elastically presses the lamp body in the clamping groove 32*a*, improving the pressing force of the pressing portion 3242 on the lamp body, and the lamp body is a physiotherapy lamp or a phototherapy lamp.

Compared with the related art, the beneficial effects of the present application are as follows:

The present application provides a lamp body bracket device 100 and a phototherapy device. The base 10 can be placed on the ground, a tabletop or a support surface. The lifting seat 20 is provided above the base 10, and the lifting seat 20 is connected to the base 10, is liftable and can lift along the up and down direction. The lifting seat 20 is provided with a support portion 21. The clamping assembly 30 includes a support bracket 31 and at least one clamping member 32, and the support bracket 31 is provided on one side of the support portion 21, connected to the support portion 21, and provided horizontally or vertically relative to the support portion 21. A height position of the support bracket 31 is adjusted along with the lifting of the lifting seat 20, and the clamping member 32 is provided on the support bracket 31 and a position of the clamping member 32 can be adjusted relative to the support bracket 31. The clamping member 32 is provided with a clamping groove 32*a* for clamping the lamp body, so as to realize the functions of lifting, moving and clamping, thereby facilitating the lamp body to be suspended in the air or placed on the ground, to be compatible with different supporting scenarios of the lamp body. And the clamping member 32 adjusts the size of the clamping groove 32*a* during movement to adapt to lamp bodies of various sizes, thereby improving the versatility of the lamp body bracket device 100.

In the above embodiments, the description of each embodiment focuses on different aspects. For parts not described in detail in a certain embodiment, reference can be made to the relevant descriptions of other embodiments.

In the description of this application, the terms “first” and “second” are only used for descriptive purposes, and cannot be understood as indicating or implying relative importance or implicitly indicating the quantity of the indicated technical features. Therefore, the features defined with “first” and “second” may explicitly or implicitly include one or more such features.

Specific examples are used herein to illustrate the principles and implementation methods of the present application. The descriptions of the above embodiments are only used to help understand the methods and core ideas of the present application, and for those skilled in the art, there will be changes in the specific implementation methods and application scopes based on the ideas of the present application. In conclusion, the content of this specification should not be understood as a limitation to the present application.

What is claimed is:

1. A lamp body bracket device, for supporting a lamp body, comprising:

a base, capable of being placed on a ground, a table top or a support surface;

a lifting seat, provided above the base, wherein the lifting seat is connected to the base, is liftable and lifts along an up and down direction, and the lifting seat is provided with a support portion; and a clamping assembly, comprising a support bracket and at least one clamping member, wherein the support bracket is provided on a side of the support portion, connected to the support portion and provided horizontally or vertically relative to the support portion;

wherein a height position of the support bracket is adjusted along with a lifting of the lifting seat, and the at least one clamping member is provided on the support bracket and a position of the at least one clamping member is adjusted relative to the support bracket, and the clamping member is provided with a clamping groove for clamping the lamp body;

wherein the clamping member comprises a clamping main body and a first installation portion; the first installation portion is connected to the clamping main body and provided on the support bracket; the first installation portion is capable of being provided at different positions of the support bracket; the clamping main body is supported by the first installation portion and provided below or above the support bracket;

the clamping main body is provided with the clamping groove, and the clamping groove has a first opening in a left-right direction and a second opening in a front-rear direction, both the first opening and the second opening are connected to the clamping groove and configured for the lamp body to pass through;

the clamping main body is provided with a first support arm and a second support arm that are provided opposite to each other in the up and down direction, and the clamping groove is formed between the first support arm and the second support arm;

the first support arm is provided below the second support arm and supports the lamp body in the clamping groove;

the clamping main body is connected with a plurality of pressing members that are provided on a same second support arm and distributed at different positions of the second support arm;

each pressing member is provided with a moving portion and a pressing portion, the moving portion is movably connected to the second support arm and is movable in the up and down direction; and the pressing portion is connected to the moving portion and located in the clamping groove, the pressing portion moves along with a movement of the moving portion and presses down the lamp body in the clamping groove, so that the pressing portion and the first support arm jointly clamp the lamp body in the clamping groove.

2. The lamp body bracket device according to claim 1, wherein two clamping members are provided opposite to each other and provided on a same support bracket;

the two clamping members are respectively located at different positions of the support bracket to be compatible with lamp bodies of different sizes;

in the two clamping members, an accommodation space is formed between two opposite clamping grooves, and the accommodation space is configured to accommodate the lamp body and allow the lamp body to be inserted in a horizontal direction.

3. The lamp body bracket device according to claim 1, wherein the support bracket is provided with a plurality of first threaded holes, the plurality of first threaded holes are provided along a length direction of the support bracket and distributed at different positions of the support bracket; the first installation portion is frame-shaped and sleeved on an outer peripheral side of the support bracket; a first through hole is provided between the first installation portion and the clamping main body, and the first through hole is configured for the support bracket to pass through; and the first installation portion is connected with a first screw, the first screw passes through the first installation portion and is screwed into one of the plurality of the first threaded hole to realize an installation of the first installation portion and the support bracket.

4. The lamp body bracket device according to claim 1, wherein the second support arm is provided with a second threaded hole, the moving portion passes through the second threaded hole, and a peripheral side wall of the moving portion is screwed into the second threaded hole; the moving portion is rotated by manual operation, moves relative to the second support arm and drives the pressing portion to press the lamp body in the clamping groove; an end of the moving portion located outside the second support arm serves as the first operating end;

or, the second support arm is provided with a first passing hole, the moving portion movably passes through the first passing hole and is movable in the up and down direction, and the end of the moving portion located outside the second support arm serves as the second operating end;

the moving portion is sleeved with an elastic member, the elastic member is located between the second support arm and the pressing portion and exerts elastic downward pressure on the pressing portion, so that the pressing portion elastically presses the lamp body in the clamping groove, and the lamp body is a physiotherapy lamp or a phototherapy lamp.

5. The lamp body bracket device according to claim 1, wherein the support portion is provided with a second through hole extending along a length direction of the support portion, and the second through hole is provided with a front opening for the support bracket to pass through, and an outer side wall of the support bracket is restricted by an inner side wall of the second through hole to maintain a current posture of the support bracket;

an end of the support bracket far away from the clamping member is provided with a third threaded hole; and the support portion is connected with a second screw, the second screw passes through the support portion and is screwed into the third threaded hole, so that an end of the second screw and the support bracket are clamped on the support portion.

6. The lamp body bracket device according to claim 1, wherein the base includes a support column, the support column is provided with a lifting hole provided in the up and down direction for the lifting seat to lift; and the support column is connected with a lifting module for driving the lifting of the lifting seat, and the lifting module is a mechanical lifting module.

7. The lamp body bracket device according to claim 6, wherein when the lifting module is a mechanical lifting module, the lifting module is provided with a fixing seat, a screw rod and a rotation handle; the fixing seat is built in the support column and fixed to the support column; the screw rod is rotatably connected to the fixing seat and is rotatable along an axis of the screw rod;

the screw rod is screwed into the lifting seat, and the screw rod drives the lifting seat to lift during rotation; the rotation handle is provided on an outer side of the support column and rotatably connected to the fixing seat; and a transmission module is provided between the rotation handle and the screw rod, and the transmission module is respectively connected to the rotation handle and the screw rod and transmits a power of the rotation handle to the screw rod, so that the screw rod rotates under a drive of the rotation handle.

8. A lamp body bracket device, for supporting a lamp body, comprising:

a base;

a lifting seat, provided above the base, wherein the lifting seat is connected to the base, is liftable and lifts along an up and down direction, and the lifting seat is provided with a support portion; and a clamping assembly, comprising a support bracket and at least one clamping member; wherein the support bracket is provided on a side of the support portion and connected to the support portion, a height position of the support bracket is adjusted along with a lifting of the lifting seat, the clamping member is provided on the support bracket, and the clamping member is configured to clamp the lamp body;

wherein the clamping member comprises a clamping main body and a first installation portion; the first installation portion is connected to the clamping main body and provided on the support bracket; the first installation portion is capable of being provided at different positions of the support bracket; the clamping main body is supported by the first installation portion and provided below or above the support bracket;

the clamping main body is provided with a clamping groove, and the clamping groove has a first opening in a left-right direction and a second opening in a front-rear direction, both the first opening and the second opening are connected to the clamping groove and configured for the lamp body to pass through;

the clamping main body is provided with a first support arm and a second support arm that are provided opposite to each other in the up and down direction, and the clamping groove is formed between the first support arm and the second support arm;

the first support arm is provided below the second support arm and supports the lamp body in the clamping groove;

the clamping main body is connected with a plurality of pressing members that are provided on a same second support arm and distributed at different positions of the second support arm;

each pressing member is provided with a moving portion and a pressing portion, the moving portion is movably connected to the second support arm and is movable in the up and down direction; and the pressing portion is connected to the moving portion and located in the clamping groove, the pressing portion moves along with a movement of the moving portion and presses down the lamp body in the clamping groove, so that the pressing portion and the first support arm jointly clamp the lamp body in the clamping groove.

9. The lamp body bracket device according to claim 8, wherein the base includes a support column, the support column is provided with a lifting hole provided in the up and down direction for the lifting seat to lift;

the support column is connected with a lifting module for driving the lifting of the lifting seat, and the lifting module is a mechanical lifting module.

10. The lamp body bracket device according to claim 9, wherein when the lifting module is a mechanical lifting module, the lifting module is provided with a fixing seat, a screw rod and a rotation handle; the fixing seat is built in the support column and fixed to the support column; the screw rod is rotatably connected to the fixing seat and is rotatable along an axis of the screw rod; the screw rod is screwed into the lifting seat, and the screw rod drives the lifting seat to lift during rotation.

11. The lamp body bracket device according to claim 10, wherein the rotation handle is provided on an outer side of the support column and rotatably connected to the fixing seat; and a transmission module is provided between the rotation handle and the screw rod, and the transmission module is respectively connected to the rotation handle and the screw rod and transmits a power of the rotation handle to the screw rod, so that the screw rod rotates under a drive of the rotation handle.

12. The lamp body bracket device according to claim 11, wherein the transmission module is a gear transmission module.

* * * * *